United States Patent [19]

Ségura

[11] Patent Number: 4,768,957
[45] Date of Patent: Sep. 6, 1988

[54] DENTURE AND FIXING DEVICE THEREFOR

[76] Inventor: Claude Ségura, 20 rue Claude Bernard, 66000 Perpignan, France

[21] Appl. No.: 935,990

[22] Filed: Nov. 28, 1986

Related U.S. Application Data

[63] Continuation-in-part of Ser. No. 785,376, Oct. 8, 1985, abandoned.

[30] Foreign Application Priority Data

Oct. 8, 1984 [FR] France ............................. 84 15378

[51] Int. Cl.⁴ ............................................. A61C 13/12
[52] U.S. Cl. .................................... 433/181; 433/177; 433/180
[58] Field of Search ............... 433/180, 181, 182, 183, 433/9, 177, 178

[56] References Cited

U.S. PATENT DOCUMENTS

| | | | |
|---|---|---|---|
| 2,889,625 | 6/1959 | Saffir | 433/180 |
| 3,076,264 | 2/1963 | Goodman | 433/178 |
| 3,216,111 | 11/1965 | Sink | 433/177 |
| 4,243,386 | 1/1981 | Kawaguchi | 433/9 |
| 4,362,509 | 12/1982 | Sule | 433/181 |
| 4,433,960 | 2/1984 | Garito et al. | 433/9 |
| 4,445,861 | 5/1984 | Klepucki | 433/9 |
| 4,479,527 | 10/1984 | Boettcher | 433/180 |
| 4,544,358 | 10/1985 | Montero | 433/181 |

FOREIGN PATENT DOCUMENTS 2085303 4/1982 United Kingdom ............... 433/181

Primary Examiner—John J. Wilson
Attorney, Agent, or Firm—Sughrue, Mion, Zinn, Macpeak, and Seas

[57] ABSTRACT

A denture-retaining male coupling portion (5) is fixed to a tab (4) which is itself glued to an inside face of an anchor tooth (1). The denture includes a metal plate having a corresponding female coupling portion (6). There is no need to use clasps or to remove healthy tissue from the anchor teeth.

3 Claims, 2 Drawing Sheets

DENTURE AND FIXING DEVICE THEREFOR

This is a continuation-in-part of application Ser. No. 785,376, filed Oct. 8, 1985, now abandoned.

The present invention relates to a fixing device for a denture, said device being without clasps.

BACKGROUND OF THE INVENTION

When a single tooth is missing, it may be replaced by a bridge comprising a false tooth anchored to the adjacent teeth which must be healthy, at least in part. Such a denture is fixed. When several teeth are missing, the conventional technique is to fit a metal plate or denture in the patient's mouth, with the plate supporting a set of false teeth. The plate bears on the maxillary cavity or on some of the remaining teeth. However, it is also necessary to anchor it to suitably strong remaining teeth. The anchorage is generally provided by means of clasps placed around healthy teeth. Unfortunately, initially healthy teeth soon decay after clasps have been fitted thereto because of contact with the metal of the clasps and because of the mechanical forces which the plate transmits to the teeth via the clasps. The teeth also tend to work loose under the effect of the lateral forces applied thereto. Further, such clasps are disagreeable to wear and unpleasant in appearance.

In order to remedy these drawbacks, proposals have already been made to replace clasps around healthy teeth by crowning the teeth to provide permanent couplings to which the plate can be removably fixed. The healthy teeth concerned are thus drilled to form a frustoconical post. An artificial crown is then cemented to the post. A part of the crown is made of metal so that a portion of a coupling (generally a male portion) can be soldered or welded thereto prior to the crown being fitted in the mouth. A larger, female portion of the coupling is fixed to the plate, thus constituting an all-metal coupling which is horizontally-releasable. It is thus possible to implant a plate in the patient's mouth without the need for clasps. Once the plate is in place, it is normally completely invisible, thus increasing the patient's mental and functional comfort, (see British patent No. 2 085 303).

This solution also has drawbacks. Firstly it requires a considerable amount of work on the part of the dentist who has to shape the teeth which support the couplings, thereby destroying a considerable quantity of healthy tissue. Secondly, given the forces which are exerted between the plate and the anchor teeth, the anchor couplings need to be replaced at relatively short intervals due to wear of the mechanical connection. By bearing against the tooth-mounted male portions, the denture very quickly causes damage.

Preferred implementations of the present invention mitigate the drawbacks of the second method described above. The invention also provides a mounting which enables the mechanical connection between the plate and the anchor teeth to be replaced extremely rapidly.

SUMMARY OF THE INVENTION

According to the present invention a plate or denture, and more particularly a device for removably fixing such a plate or denture on two healthy teeth, comprises two separate elements each fixable to respective a healthy tooth by gluing, and a main one-piece denture portion provided with integral elements for co-operating with said separate elements, each of said separate elements comprising a ball-shaped male portion fixed to a tab which is in turn fixable by glue to a healthy tooth, and each of said integral elements comprising a female portion which is cylindrical in shape and capable of being threaded over one of said balls, each of said cylindrical portions being bottomless in order to avoid bearing against the corresponding ball. Under such conditions, the ball-cylinder connectors serve to determine the position of the denture in the mouth of the user but do not serve to transmit masticatory forces. These forces are transmitted by the mucous and optionally also by lugs fixed to the denture and bearing against healthy teeth.

It is thus no longer necessary to drill away healthy tissue in order to crown the teeth to which the denture is to be anchored. An anchor point is fixed to a tooth in a manner which is invisible (i.e. the anchor point is on a hidden face of the tooth), and it is fixed by means of a cyanoacrylate-based glue which provides a mechanical connection which is capable of holding the plate fixed inside the mouth in such a manner that the patient is unaware of its presence after a very short period of getting used to it.

Preferably the inside of the female portion is provided with a lining of elastically deformable material (plastic) so as to provide the denture with play-free fixing, and to avoid wear on the metal parts.

In this manner, the metal-on-metal contact that leads to rapid wear is replaced by metal-on-plastic contact. As a result, the mechanical connection benefits from the flexibility provided by the plastic, and when the plastic does eventually wear out, it is easily replaced: in about 1 minute.

In an advantageous embodiment of the invention, the ballsupporting tab is curved and surrounds a portion of the tooth to which it is glued, thereby improving fixing by performing the function of a clasp. It is possible for the tabs to include curved extensions passing over the teeth in order to serve as a bearing surfaces for the lugs which bear on healthy teeth.

BRIEF DESCRIPTION OF THE DRAWING

Embodiments of the invention are described by way of example with reference to the accompanying drawings, in which.

MORE DETAILED DESCRIPTION

The present invention relates to fixing a denture comprising a set of teeth, and it is not suitable for replacing a single tooth. Various techniques exist for replacing a single tooth and they do not concern the present invention.

Figure 1:
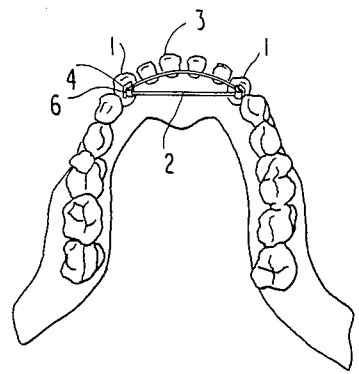
FIG. 1 is a perspective view of a mandible on which a dental prosthesis in accordance with the invention has been fitted.

FIG. 1 shows a mandible which retains at least two healthy teeth 1 suitable for anchoring a plate 2. The plate 2 has a row of false teeth 3 fixed thereon to mask a sector of missing teeth between the said teeth 1.

Figure 2B:
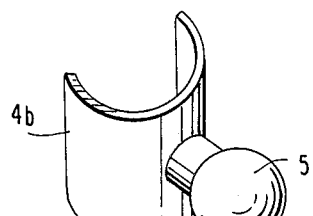
FIGS. 2A and 2B are perspective views showing how an anchor point coupling is fixed to a tooth.
Figure 2A:
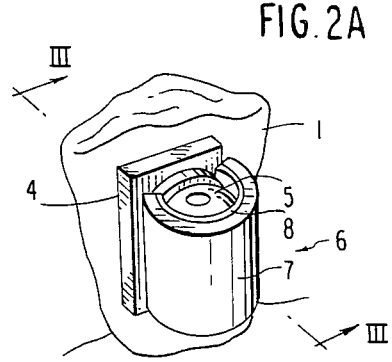

As can be seen in FIG. 2, each of said teeth 1 has a cast metal tab 4 glued against the inside face of the tooth by means of a suitable resin. Prior to being glued in place, each tab 4 is preferably subjected to electrolytic mordanting in order to increase its effective surface area and thus improve its adherence on the corresponding tooth face. An anchor point coupling 5 is soldered or welded to the tab 4 and acts as the male portion of a ball-and-socket type assembly having a female portion 6 which is fixed to the plate 2 (see FIG. 1).

In accordance with the invention, the coupling 5 is constituted by a ball and the female portion 6 is constituted by a hollow cylinder. Thus, the female portion 6 is free to pivot on the ball, which is advantageous, not only while the denture is being put into place, but also leaves enough play to prevent excess force being applied to the teeth 1, which would tend to work loose if fitted with clasps.

In accordance with a characteristic of the invention, the female portion 6 is constituted by a metal tube 7 which is split along a generator line in order allow it to be threaded over the ball 5, and the inside of the metal tube is lined with a plastic sleeve 8. This prevents metal-on-metal contact which would lead to rapid wear. Preferably, the inside diameter of the sleeve 8 is slightly less than the diameter of the ball 5. The plate is put into position by applying sufficient force to deform the plastic, which may have holes passing therethrough in order to facilitate creep and to improve plate retention. When the ball reaches its final or operative position, the plastic tends to creep around the ball, thereby automatically forming a seat for the ball.

High pressure grade polyethylene, or some other biocompatible plastic may be used. If the connection becomes worn, the plate can easily be removed and a new lining 8 installed in place of the worn lining. There is no longer any need to act on the ball 5 or on the socket 6.

The diameter of the ball 5 is advantageously in the range 1.1 mm to 2.5 mm and is preferably about 1.8 mm. The lining 8 has a thickness of 0.8 mm to 1.2 mm and the inside diameter of the lining is less than the outside diameter of the ball by an amount lying in the range 0.1 mm to 0.3 mm, and preferably by 0.2 mm.

FIG. 2B shows a variant in which the tab 4b partially surrounds the tooth, thereby providing fastening equivalent to that provided by a clasp. The tab 4b is glued to the tooth over its entire surface area in contact therewith, thus preventing the ingress of dirt between the metal and the tooth. The tooth is not mutilated and no hard tissue is destroyed. The tab 4b may also include a curved extension 41 passing over the top of the tooth, as shown in FIG. 5 and for reasons explained below.

Figure 3:
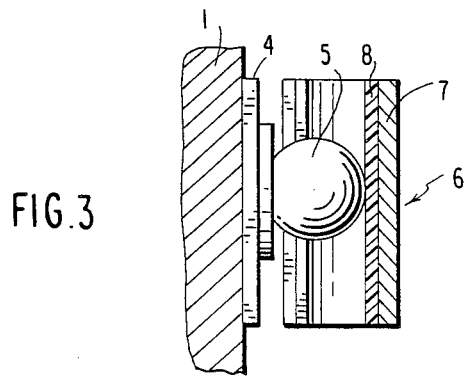
FIG. 3 is a section of a line III—III in FIG. 2A.

In the embodiment of the invention shown in FIGS. 1 to 3, the denture is held during mastication solely by the mucous of the jaw (it constitutes a mucous-supported denture). This leads to fatigue of the mucous and may lead to sores. In which cases wearing and using the denture become painful.

Figure 4:
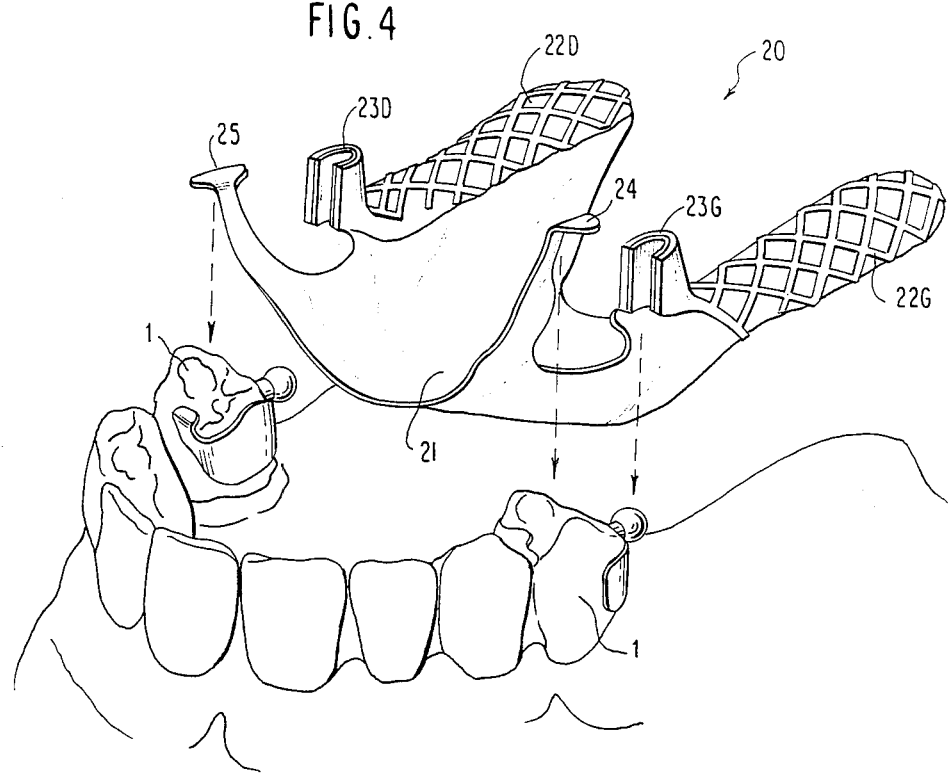
FIG. 4 is a perspective view of another embodiment of the invention with the denture being shown slightly removed from its position in normal use.
Figure 5:
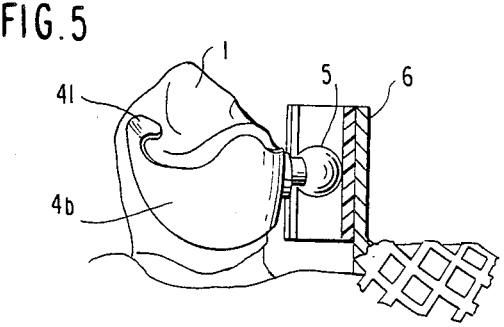
FIG. 5 is a section view showing a detail of the fixing for the FIG. 4 denture.

The denture shown in FIGS. 4 and 5 is likewise supported by healthy teeth. It is intended to replace the bottom molars on both sides. It comprises a metal part 20 including an interconnecting bridge 21, and two rear portions 22D and 22G which are provided to bear against the jaws and to receive false teeth made of ceramics, metal, or plastic. The integral female link elements 23G and 23D analogous to the above-described elements 6 are fixed thereto. This denture further includes lugs 24 and 25 for bearing against healthy teeth in order to support the front portion of the denture during mastication, since no support can be provided via the ball connections 5–6 which serve solely to hold the denture in position. In order to avoid damaging healthy teeth, these lugs bear against extensions 41 of the tabs, which extensions are folded back over the healthy teeth 1, as explained above with reference to FIG. 5. Under these conditions, the lugs 24 and 25 do not damage the healthy teeth. Naturally, the extensions 41 are glued onto to the teeth 1 in order avoid ingress of dirt between the metal and the tooth.

The female cylindrical portions 6 are described as being "bottomless" since the ball or male portion must not receive a thrust force. However, the top end of the female portion may be closed in order to prevent dirt from entering into the tubular portion, but under no circumstances may the ball or male portion come into contact with the closure whose function is solely to keep the inside of the connection clean.

A plate in accordance with the invention is fitted as follows:

After the plate has been fabricated, cast tabs 4 having male coupling portions 5 soldered or welded thereto are glued to the anchor teeth. Alternatively, the male portions may be integrally cast with the tabs, e.g. in stainless steel. The female portions 6 are then placed over the balls and the plate takes up its position of use inside the mouth.

I claim:

1. A device for removably fixing a denture on two healthy teeth, the device comprising a main one-piece portion and two separate fixing elements, each of said fixing elements being fixable on a healthy tooth by gluing, and said main one-piece portion comprising two integral fixing elements which cooperate with said separate fixing elements, each of said separate fixing elements comprising a fixing tab and a ball-shaped male portion which is fixed to said fixing tab which is in turn fixable by gluing to a healthy tooth, wherein the fixing tab of the male portion of each of said separate fixing elements includes an extension curved over the top of the healthy tooth and adapted to be glued thereto, with said main one-piece portion including a lug for bearing against said curved extension when the denture is in place in the mouth of the user, and each of said integral fixing elements comprising a cylindrically shaped female portion capable of being fitted over a corresponding one of said balls, said cylindrical portions being bottomless in order to avoid bearing against said ball.

2. A device according to claim 1, wherein the inside of each female portion is lined with plastic.

3. A device according to claim 2, wherein the outside diameter of each ball lies in the range 1.1 mm to 2.5 mm, the thickness of each lining lies in the range 0.8 mm to 1.2 mm, and the inside diameter of each lining is less than the outside diameter of the corresponding ball by a thickness lying in the range 0.1 to 0.3 mm.

* * * * *